(12) United States Patent
Baek et al.

(10) Patent No.: US 12,415,175 B2
(45) Date of Patent: Sep. 16, 2025

(54) SUPPORTED CATALYST FOR BUTANE HYDROGENOLYIS, METHOD OF PRODUCING THE SUPPORTED CATALYST AND METHOD TO PRODUCE ETHANE

(71) Applicant: SABIC Global Technologies B.V., Bergen op Zoom (NL)

(72) Inventors: Byeongjin Baek, Sugar Land, TX (US); Istvan Lengyel, Sugar Land, TX (US); Katherine Barton, Sugar Land, TX (US); Neeta Kulkarni, Sugar Land, TX (US); Dustin Fickel, Sugar Land, TX (US)

(73) Assignee: SABIC Global Technologies B.V., Bergen op Zoom (NL)

( * ) Notice: Subject to any disclaimer, the term of this patent is extended or adjusted under 35 U.S.C. 154(b) by 460 days.

(21) Appl. No.: 17/995,320

(22) PCT Filed: Feb. 24, 2021

(86) PCT No.: PCT/IB2021/051549
§ 371 (c)(1),
(2) Date: Oct. 3, 2022

(87) PCT Pub. No.: WO2021/224691
PCT Pub. Date: Nov. 11, 2021

(65) Prior Publication Data
US 2023/0226522 A1    Jul. 20, 2023

Related U.S. Application Data

(60) Provisional application No. 63/022,124, filed on May 8, 2020.

(51) Int. Cl.
*B01J 21/04* (2006.01)
*B01J 23/652* (2006.01)
(Continued)

(52) U.S. Cl.
CPC ........... *B01J 21/04* (2013.01); *B01J 23/6525* (2013.01); *B01J 35/613* (2024.01); *B01J 35/615* (2024.01);
(Continued)

(58) Field of Classification Search
CPC ........ B01J 21/04; B01J 35/615; B01J 35/613; B01J 23/6525; B01J 37/0207;
(Continued)

(56) References Cited

U.S. PATENT DOCUMENTS 4,140,621 A    2/1979    Franck et al.
6,350,922 B1 *    2/2002    Vosejpka .............. C07C 29/141
568/842

(Continued)

FOREIGN PATENT DOCUMENTS

CA    1123418    5/1982
CN    102911011    2/2013
(Continued)

OTHER PUBLICATIONS

Lele Jin et al., "High performance of Mo-promoted Ir/SiO2 catalysts combined with HZSM-5 toward the conversion of cellulose to C5/C6 alkanes." Bioresource Technology 297, pp. 1-8. (Year: 2020).*

(Continued)

*Primary Examiner* — Patricia L. Hailey
(74) *Attorney, Agent, or Firm* — Norton Rose Fulbright US LLP

(57) ABSTRACT

Catalysts for the hydrogenolysis of butane are described. A supported catalyst for hydrogenolysis of butane to ethane can include a support and a catalytic crystalline bimetallic composition that can include a molybdenum-iridium (Mo—Ir) crystalline composition attached to the support. The supported catalyst has a BET specific surface area of at least
(Continued)

100 m²/g, preferably 100 m²/g to 500 m²/g. Method of use and methods of making the catalyst are also described.

20 Claims, 1 Drawing Sheet

(51) Int. Cl.
- B01J 35/61 (2024.01)
- B01J 37/02 (2006.01)
- B01J 37/08 (2006.01)
- C07C 4/10 (2006.01)

(52) U.S. Cl.
CPC ....... *B01J 37/0207* (2013.01); *B01J 37/0236* (2013.01); *B01J 37/08* (2013.01); *C07C 4/10* (2013.01); *B01J 2531/64* (2013.01); *B01J 2531/827* (2013.01); *C07C 2521/04* (2013.01); *C07C 2523/652* (2013.01)

(58) Field of Classification Search
CPC .... B01J 37/0236; B01J 37/05; B01J 2531/64; B01J 2531/827; C07C 4/10; C07C 2521/04; C07C 2523/652
USPC ........ 502/355, 313, 321, 322; 420/429, 461; 585/648, 653
See application file for complete search history.

(56) References Cited

U.S. PATENT DOCUMENTS

| | | | |
|---|---|---|---|
| 6,781,022 | B1 | 8/2004 | Katrib et al. |
| 7,473,814 | B2 | 1/2009 | Basset et al. |
| 12,252,466 | B2 * | 3/2025 | Fickel ................ C07C 5/03 |
| 2016/0136632 | A1 * | 5/2016 | Monnier ................ B01J 23/40 502/313 |
| 2018/0361357 | A1 | 12/2018 | De Vlieger et al. |
| 2021/0269381 | A1 * | 9/2021 | Fickel ................ C07C 4/10 |
| 2021/0316285 | A1 * | 10/2021 | Dasari ................ B01J 29/0358 |
| 2021/0331988 | A1 * | 10/2021 | Fickel ................ C07C 4/06 |

FOREIGN PATENT DOCUMENTS

| | | | |
|---|---|---|---|
| CN | 106536456 | 3/2017 | |
| FR | 2346309 | 10/1977 | |
| FR | 2346309 A1 * | 10/1977 | .............. B01J 23/46 |
| FR | 2782933 | 11/2000 | |
| WO | WO-2011126545 A1 * | 10/2011 | ............ B01J 23/002 |
| WO | WO 2020/061010 | 3/2020 | |
| WO | WO 2020/061011 | 3/2020 | |
| WO | WO 2020/061012 | 3/2020 | |

OTHER PUBLICATIONS

Bernard, et al., "A Selective Route for the Hydrogenolysis of Alkanes into Ethane", *Studies in Surface Science and Catalysis*, 7(A), 149-159, 1981.
Buchwalter et al., "Multimetallic Catalysis Based on Heterometallic Complexes and Clusters", *Chemical Reviews*, 115, 28-126, 2015.
Engstrom, et al., "The Hydrogenolysis of Alkanes over Single-Crystalline Surfaces of Iridium: The Influence of Surface Structure on the Catalytic Selectivity", *J. Vac. Sci. Technol.*, 5, 825-827, 1987.
Goodman, D.W., "Structure/reactivity Relationships for Alkane Dissociation and Hydrogenolysis Using Single Crystal Kinetics", *Catal. Today*, 12(2-3), 189-199, 1992.
International Search Report in corresponding PCT Application No. PCT/IB2021/051549, mailed May 10, 2021.
Lee, J. S. et al., "Molybdenum carbide catalysts 3. Turnover rates for the hydrogenolysis of n-butane", *Journal of Catalysis*, 125, 157-170, 1990.
Nakamura, R. et al., "The hydrogenolysis of alkanes on Mo(0)Al$_2$O$_3$ catalysts", *Journal of Catalysis*, 93(2), 399-408, 1985.
Shapley et al., "Bimetallic Catalysts from Alumina-Supported Molybdenum-Iridium Clusters", *J. Phys. Chem.*, 94(3), 1190-1196, 1990.
Office Action issued in corresponding Chinese Application No. 202180031910.4, dated May 8, 2025 (English Translation provided).

* cited by examiner

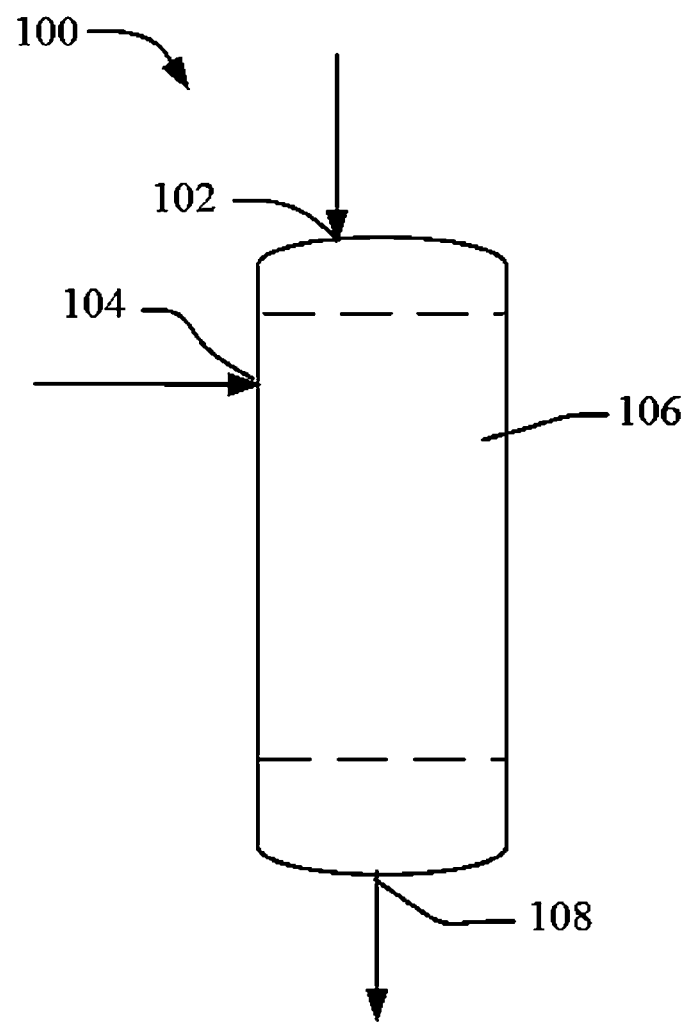

SUPPORTED CATALYST FOR BUTANE HYDROGENOLYIS, METHOD OF PRODUCING THE SUPPORTED CATALYST AND METHOD TO PRODUCE ETHANE

CROSS REFERENCE TO RELATED APPLICATIONS

This application is a national phase application under 35 U.S.C. § 371 of International Application No. PCT/IB2021/051549 filed Feb. 24, 2021, which claims the benefit of priority of U.S. Provisional Patent Application No. 63/022,124 filed May 8, 2020, which are hereby incorporated by reference in their entirety.

BACKGROUND OF THE INVENTION

A. Field of the Invention

The invention generally concerns supported catalysts for hydrogenolysis of butane to ethane. A supported catalyst of the present invention can have a BET surface area of at least 100 m²/g and include a crystalline catalytic bimetallic composition attached to a support.

B. Description of Related Art

Light alkanes, particularly ethylene, can be obtained through a butane (C4) steam cracking process. However, steam cracking of a butane feedstock can produce a relatively low yield of ethylene. A combination of butane hydrogenolysis and steam cracking selectively can produce desired olefins. In some instances, hydrogenolysis reaction can be advantageous. The hydrogenolysis of butanes is shown in reaction schemes 1-3, which can result in methane, ethane and propane

  (1)

  (2)

  (3)

Reaction scheme 1 is the desired hydrogenolysis reaction, while reaction schemes 2 and 3 show the side reactions.

In the hydrogenolysis of butane reaction it is desirable for butane hydrogenolysis catalyst to have selectivity toward ethane to minimize the carbon loss to byproducts (e.g., methane and propane). Conventional iridium (Ir) based catalysts can have an ethane selectivity of 60-70% at a butane conversion level of about 80-90%. However, such catalysts suffer in that the reaction is only attainable at high temperature (e.g., greater than 300° C.), which can jeopardize the safety of reactor operation and potentially lead to thermal runaway due to the exothermic nature of the reaction. In addition, the use of noble metals such as Ir and platinum (Pt) can result in significant capital cost. For example, Ir is not readily available and can be difficult to recover from a spent catalyst.

Various attempts to produce cost effective butane hydrogenolysis catalysts with high ethane selectivity have been described. For example, Shapley etaL. (J. Phys. Chem. 1990, 94, 1190-1196) describes organometallic clusters such as $CpMoIr_3(CO)$, $Cp_2Mo_2Ir_3(CO)_{10}$ on fumed alumina (where Cp is $n^5$-$C_5H_5$) for butane hydrogenolysis catalysis at 215° C. with a ethane selectivity of 70%. This catalyst suffers in that butane conversion was less than 5 wt. % at this temperature.

While attempts to produce butane hydrogenolysis catalysts have been described, there is still a need for cost effective catalysts with high ethane selectivity and high butane conversion.

SUMMARY OF THE INVENTION

A solution to at least one problem associated with high temperature operation of butane hydrogenolysis has been discovered. At least one solution includes the use of a crystalline catalytic bimetallic composition that includes a molybdenum and iridium (Mo—Ir) crystalline composition attached to a support. The catalyst can have a specific surface area of at least 100 m²/g, preferably 100 m²/g to 500 m²/g, as measured using BET methodology. The catalyst can have a hydrogenolysis of butane to ethane selectivity of at least 50%, preferably 70%, most preferably 75%. The catalyst can have a butane conversion of at least 50% at a reaction temperature of 240 to 325° C. Notably, the crystalline catalytic bimetallic composition does not require organic ligands to stabilize the metals. The catalyst of the present invention can also have a carbon binding energy approximate to the carbon-carbon binding energy on a Columns 8 and 9 noble metal, preferably Ir metal as determined using DFT calculations.

In one aspect of the present invention, supported catalysts for hydrogenolysis of butane are described. A supported butane hydrogenolysis catalyst can include a support, and a catalytic crystalline bimetallic composition that includes a molybdenum-iridium (Mo—Ir) crystalline composition attached to the support. The supported catalyst can have a BET specific surface area of at least 100 m²/g, preferably 100 m²/g to 500 m²/g. The particle size of the catalytic crystalline bimetallic composition can range from 1 to 10 nm or any value or range there between (e.g., 1, 2, 3, 4, 5, 6, 7, 8, 9, 10 nm) as determined using chemisorption methodology or microscopy. The support can include alumina ($Al_2O_3$), a zeolite, titania ($TiO_2$), or silica ($SiO_2$), or a combination thereof. In a preferred embodiment, the crystalline catalytic Mo—Ir composition does not include organic ligands, preferably cyclopentadiene ligands. Said another way, the crystalline catalytic Mo—Ir composition is free of organic ligands, preferably cyclopentadiene ligands. The catalyst can include 0.1 wt. % to 5 wt. % of total crystalline MoIr composition, preferably 0.1 wt. % to 3 wt. %, or any range or value there between (e.g., 0.1, 0.5, 1, 1.5, 2.0, 2.5, 3.0, 3.5, 4.0, 4.5, and 5 wt. %). A Mo:Ir molar ratio can range from 1:3 to 4:1 or any range or value there between, preferably 1:3. The crystalline catalytic Mo—Ir composition can include a $MoIr_3$ crystalline structure, a $Mo_3Ir$ crystalline structure, or a $MoIr_4$ crystalline structure, or a mixture thereof. A non-limiting example of the supported catalyst of the present invention is 0.1 wt. % to 5 wt. % of $MoIr_3$, preferably 0.6 wt. % of $MoIr_3$ on an $Al_2O_3$ support, preferably gamma-$Al_2O_3$.

In another aspect of the present invention, methods of producing ethane are described. A method to produce ethane can include contacting the supported butane hydrogenolysis catalyst of the present invention with butane under conditions sufficient for hydrogenolysis of butane (e.g., n-butane or a mixture of iso-butane and n-butane) and produce ethane. Contacting conditions can include a temperature of 240° C. to 325° C., preferably 260° C. to 300° C., a pressure of 0.35 MPa to 1.4 MPa, a weight hourly space velocity (WHSV) of 1 to 10 hr⁻¹, preferably 1 to 4 hr⁻¹, or combinations thereof. Under the contacting conditions, the supported catalyst can have an ethane selectivity of at least 70%, preferably 50 to 90%, more preferably 70% to 80%, or most preferably about 75%. In some embodiments, the butane conversion is at least 50%, preferably 50 to 95%, more preferably 70 to 90% at a reaction temperature of 240° C. to 325° C. As exemplified in the Examples, in a non-limiting manner, the catalyst of the present invention can have a butane conversion at least 5 times greater, preferably 10 time greater than a comparative Ir catalyst at the same reaction conditions and same total weight percentage of catalytic metal in the catalyst.

In yet another aspect of the present invention, methods of producing the supported catalysts of the present invention are described. A method can include impregnating a support with a catalytic Mo—Ir precursor composition to form an impregnated support/Mo—Ir precursor composition material, and heat-treating drying the impregnated support/Mo—Ir precursor composition material to from the supported crystalline Mo—Ir catalyst of the present invention. The support can include gamma-alumina extrudates, a zeolite (e.g., ZSM-5), titania extrudates, silica extrudates, or a mixture thereof. In some embodiments, impregnating can include adding the catalytic metal precursor composition dropwise onto the support and agitating the impregnated support/catalytic metal precursor composition for 2 to 24 hours. Heat-treating can include drying the impregnated support/catalytic metal precursor composition at a temperature of 85° C. to 100° C. for 2 to 24 hours, and calcining the dried impregnated support/catalytic metal precursor at a temperature of 275° C. to 350° C.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to other aspects of the invention. It is contemplated that any embodiment or aspect discussed herein can be combined with other embodiments or aspects discussed herein and/or implemented with respect to any method or composition of the invention, and vice versa. Furthermore, compositions of the invention can be used to achieve methods of the invention.

The following includes definitions of various terms and phrases used throughout this specification.

The terms "about" or "approximately" are defined as being close to as understood by one of ordinary skill in the art. In one non-limiting embodiment, the terms are defined to be within 10%, preferably within 5%, more preferably within 1%, and most preferably within 0.5%.

The terms "wt. %," "vol. %," or "mol. %" refers to a weight percentage of a component, a volume percentage of a component, or molar percentage of a component, respectively, based on the total weight, the total volume of material, or total moles, that includes the component. In a non-limiting example, 10 grams of component in 100 grams of the material is 10 wt. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the words "a" or "an" when used in conjunction with any of the terms "comprising," "including," "containing," or "having" in the claims, or the specification, may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The catalysts of the present invention can "comprise," "consist essentially of," or "consist of" particular ingredients, components, compositions, etc. disclosed throughout the specification. With respect to the transitional phrase "consisting essentially of," in one non-limiting aspect, a basic and novel characteristic of the catalysts of the present invention are their abilities to catalyze hydrogenolysis of butane to produce ethane.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

Advantages of the present invention may become apparent to those skilled in the art with the benefit of the following detailed description and upon reference to the accompanying drawings.

FIG. 1 is an illustration of a reactor system to produce ethane using the butane hydrogenolysis catalyst of the present invention.

While the invention is susceptible to various modifications and alternative forms, specific embodiments thereof are shown by way of example in the drawings. The drawings may not be to scale.

DETAILED DESCRIPTION OF THE INVENTION

At least one solution to the problems associated with converting butane to ethane has been discovered. The solution can include a cost-effective catalyst that has a carbon binding energy approximate to the carbon binding energy on Ir metal. The catalyst can include a crystalline Column 6 metal/Ir composition attached to a support. Preferably, the catalyst includes a catalytic bimetallic (e.g., Mo—Ir) composition attached to a support.

These and other non-limiting aspects of the present invention are discussed in further detail in the following sections.

A. Catalyst

The catalyst of the present invention can include a support and a catalytic bimetallic composition. The catalyst can have a specific surface area of at least 100 $m^2/g$, or 100 $m^2/g$ to 500 $m^2/g$, or 100 $m^2/g$, 150 $m^2/g$, 200 $m^2/g$, 250 $m^2/g$, 300 $m^2/g$, 350 $m^2/g$, 400 $m^2/g$, 450 $m^2/g$, or 500 $m^2/g$, or any value or range there between. The support can be alumina ($Al_2O_3$), titania ($TiO_2$), silica ($SiO_2$), a zeolite, or mixtures, or combinations thereof. Non-limiting examples of zeolites include ZSM-5, ZSM-11, Y, high-silica Y, USY, EU-1, EU-2, beta, L, ferrierite, CHA, SSZ-16, Nu-3, sigma-1, silicalite-1, and combinations thereof. In some embodiments, the zeolite is ZSM-5. In a preferred embodiment, the support is gamma-$Al_2O_3$. The catalytic bimetallic composition can include crystalline catalytic Mo—Ir, Ir-platinum (Pt), and Ir/Ti compositions. In a preferred embodiment, crystalline catalytic Mo—Ir compositions can be used. The total molar ratio of Mo—Ir in the catalyst can range from 1:3 to 4:1, or 1:3, 2:3, 2:1, 3:1, or 4:1, or any range or value there between. In a preferred instance, the total molar ratio of Mo—Ir in the catalyst is 1:3. The total amount of crystalline catalytic bimetallic composition (e.g., crystalline Mo—Ir material) can range from 0.1 wt. % to 5 wt. %, or 0.2 to 1 wt. %, or 0.1, 0.2, 0.3, 0.4, 0.5, 0.6, 0.7, 0.8, 0.9, 1.0, 1.5, 2.0, 2.5, 3.0, 3.5, 4.0, 4.5, or 5 wt. % or any range or value there between. In a preferred instance, the total amount of crystalline catalytic bimetallic composition can be about 0.55 to 0.65 or about 0.6 wt. %. The particle size of the crystalline catalytic bimetallic composition can range from 1 to 10 nm, or 1, 2, 3, 4, 5, 6, 7, 8, 9, 10 nm or any range or value there between. When the crystalline catalytic bimetallic composition includes Mo—Ir crystalline compositions, it can include a $MoIr_3$ crystalline structure, a $Mo_3Ir$ crystalline structure, or a $MoIr_4$ crystalline structure, or a mixture of $MoIr_3$, $Mo_3Ir$, and $MoIr_4$ crystalline structures. These structures can each be attached to the support. The crystalline catalytic bimetallic composition (e.g., crystalline Mo—Ir compositions) can be attached to the surface of the metal oxide or zeolite surface or part of the crystal lattice of the catalyst. The attachment can be through chemical bonds. In particular instances, the bonds can be M—O bonds (where M is a metal from the catalyst and O is an oxygen from the support). The crystalline catalytic bimetallic composition is free of organic ligands (e.g., non-detectable or 0 to 0.001 wt %). In one embodiment, the crystalline Mo—Ir catalyst is free of cyclopentadiene ligands.

The catalyst can be made using impregnation methodology. In a preferred aspect, incipient wetness impregnation methodology can be used. Catalytic metal precursors can be dissolved in deionized water to form individual catalytic metal precursor solutions. Catalytic metal precursors can be obtained as a metal nitrate, a metal amine, a metal chloride, a metal coordination complex, a metal sulfate, a metal phosphate hydrate, metal complex, or any combination thereof. Examples of metal precursor compounds include hexachloroiridic acid and ammonium heptamolybdate. These metals or metal compounds can be purchased from any chemical supplier such as Sigma-Aldrich (St. Louis, Missouri, USA), Alfa-Aeaser (Ward Hill, Massachusetts, USA), and Strem Chemicals (Newburyport, Massachusetts, USA). The two solutions can be mixed to form a combined catalytic metal precursor solution or used separately. The catalytic metal precursor solutions or combined catalytic metal precursor solution can be added to a known quantity of support (e.g., weighed alumina extrudates) and agitated for a period of time (e.g., 2 to 24 hours) at ambient temperature (e.g., 20° C. to 35° C.) to form a catalytic metal precursor/support composition. The water can be removed by drying the catalytic metal precursor/support composition at a temperature of 80° C. to 100° C., or about 90° C. Once dried, the catalytic metal precursor/support composition can be calcined in air at 275° C. to 350° C. or 275° C. to 285° C. or any range or value there between. Calcination of the catalytic metal precursor/support composition forms the catalytic crystalline bimetallic composition and attaches the composition to the support.

B. Methods of Producing Ethane from Butane

FIG. 1 depicts a schematic for a process for the hydrogenolysis of butane with one reactor using the catalyst of the present invention. Reactor 100 can include inlet 102 for a $H_2$ reactant feed, inlet 104 for a butane reactant feed, reaction zone 106 (e.g., a fixed-bed reactor) that is configured to be in fluid communication with the inlets 102 and 104, and outlet 108 configured to be in fluid communication with the reaction zone 106 and configured to remove the hydrogenolysis product stream from the reaction zone. The reaction zone 106 can include the hydrogenolysis catalyst of the present invention. The $H_2$ reactant feed can enter the reaction zone 106 via the inlet 102. The reactant feed can be a mixture of butanes (e.g., isobutane and n-butane). In some embodiments, the $H_2$ reactant feed and/or the butane reactant feed can be used to maintain a pressure in the reaction zone 106. In some embodiments, the reactant feed streams include propane or trace C5s (e.g., hydrocarbons containing 5 carbon atoms). In some embodiments, the reactant feeds are premixed and provided at the same time. In some embodiments, the reactant feed can be provided in stages from $H_2$ rich to the desired $H_2$ to hydrocarbon ratio. The product stream can be removed from the reaction zone 106 via product outlet 108. The product stream can be sent to other processing units (e.g., separation units, isomerization units, and the like), stored, and/or transported.

Reactor 100 can include one or more heating and/or cooling devices (e.g., insulation, electrical heaters, jacketed heat exchangers in the wall) or controllers (e.g., computers, flow valves, automated values, etc.) that can be used to control the reaction temperature and pressure of the reaction mixture. While only one reactor is shown, it should be understood that multiple reactors can be housed in one unit or a plurality of reactors housed in one heat transfer unit. In some embodiments, a series of physically separated reactors with interstage cooling/heating devices, including heat exchangers, furnaces, fired heaters, and the like can be used.

The temperature, pressure, and WHSV can be varied depending on the reaction to be performed and is within the skill of a person performing the reaction (e.g., an engineer or chemist). Temperatures can range from 240° C. to about 325° C., 250° C. to 300° C., 270° C. to 290° C., or any value or range there between. Pressures can range from about 0.35 MPa to 1.4 MPa or 0.35, 0.40, 0.45, 0.50, 0.55, 0.60, 0.65, 0.70, 0.75, 0.8, 0.85, 0.9, 0.95, 1.0, 1.1, 1.2, 1.3, 1.4 or any range or value there between. A butane WHSV can range from 1 to 10 $hr^{-1}$, or 1, 2, 3, 4, 5, 6, 7, 8, 9, 10 $hr^{-1}$ or any range or value there between.

The product stream can include methane, propane, ethane, and unreacted reactants. The products can be separated using known separation methodology. Produced methane can be used as a fuel for the system or can be reacted with steam to make hydrogen. Produced ethane can be sent to other processing units, for example sent to a steam cracker to produce ethylene. Produced propane can be sent to other processing units, for example, sent to a cracking unit together with ethane or used for on-purpose propylene production through propane dehydrogenation. Unreacted butane and/or hydrogen can be recycled to the reactor. In some embodiments, the unreacted butane that is includes isobutane can be sent to a reverse-isomerization unit to increase the amount of n-butane in the unreacted feed stream.

Using the catalyst of the present invention, the ethane selectivity can be at least 70%, 50 to 90%, 70% to 80%, or 70%, 75%, 80%, 85%, 90%, or any value or range there between. In a preferred embodiment, the ethane selectivity is at least about 75%. In some embodiments, butane conversion can at least 50%, 50 to 95%, 70 to 90%, or at least 50%, 55%, 60%, 65%, 70%, 75%, 80%, 85% or 90%, or any value or range there between at a reaction temperature of 240° C. to 290° C.

EXAMPLES

The present invention will be described in greater detail by way of specific examples. The following examples are offered for illustrative purposes only, and are not intended to limit the invention in any manner. Those of skill in the art will readily recognize a variety of noncritical parameters which can be changed or modified to yield essentially the same results.

Example 1

Synthesis of Mo—Ir/Alumina Catalysts $H_2IrCl_6 \cdot (6H_2O)$ (0.14 g, 0.51%, MilliporeSigma, USA) and $(NH_4)_6Mo_7O_{24} \cdot (4H_2O)$ (0.02 g, 0.07%, MilliporeSigma) separately were dissolved in deionized water (5 mL) each. Each solution was thoroughly stirred and then mixed together. The mixture solution was added dropwise to weighted γ-alumina extrudates (10.0 g, Sasol, SG 6173, South Africa) and stirred for 3 hours at room temperature (25° C.). The extrudates then were dried in the oven at 90° C. for 3 hours, followed by calcination at 280° C. to produce a $MoIr_3$ (0.6 wt %)/$Al_2O_3$ catalyst.

Example 2

Synthesis of Ir/Alumina Comparative Catalyst $H_2IrCl_6 \cdot (6H_2O)$ (0.161 g, 0.80%) was dissolved in deionized water (5 mL). The solution was added dropwise to weighted γ-alumina extrudates (10 g) and stirred for 3 hours at room temperature (30° C.). The extrudates then were dried in the oven at 90° C. for 3 hours, followed by calcination at 280° C. to produce Ir (0.6 wt %)/$Al_2O_3$ catalyst.

Example 3

Method to Produce Ethane Via Butane Hydrogenolysis

The inventive catalyst (Example 1, $MoIr_3$ (0.6 wt %)/$Al_2O_3$) and the comparative catalyst (Example 2, Ir (0.6 wt %)/$Al_2O_3$) were tested under the same conditions. Testing was completed under isothermal conditions in a ½" O.D. (wall thickness 0.049")×20" length seamless 316 stainless steel reactor tube heated by a 21", three-zone Applied Test Systems (ATS) clamshell furnace. The reactor tube was fitted with an internal ⅛" seven-point thermocouple probe (Omega) to control furnace heating and monitor the temperature across the catalyst bed. The hydrocarbon feed (Airgas Research Grade) was introduced to the system as a liquid via a low-flow mini Coriolis mass flow meter (Bronkhorst model M12, 0-50 g hr-1), while the hydrogen (Praxair UHP) was introduced via a thermal mass flow controller (Brooks, model 5850E, 0-1000 sccm). The hydrocarbons were vaporized and the feeds were mixed upstream of the reactor at 140-150° C. A backpressure regulator (0-700 psig) located downstream of the reactor controlled the pressure of the system. The reactor bed was composed of three 4" layers: a central catalyst bed diluted with silicon carbide (Greystar, 30 grit) and silicon carbide layers on both sides. Approximately ⅛" of silanized glass wool (Supelco 20410) divided and supported each layer. The reactor bed was loaded such that the catalyst bed layer resided entirely within the central zone isothermal zone of the furnace. Three of the five internal thermocouple points were located at the top, middle, and bottom of the catalyst bed. In general, the ΔT across these three points was <1° C. Reaction conditions were WHSV=4 hr$^{-1}$, $H_2$/HC=2.5, the butane feed has an i-$C_4H_{10}$:n-$C_4H_{10}$ ratio of 3:7. Reaction temperatures ranged from 250° C. to 300° C.

Results of the runs are listed in Table 1 At the temperature of 250° C., the inventive catalyst ($MoIr_3$/$Al_2O_3$) showed almost 10 times higher catalytic activity compared to the comparative catalyst (Ir/$Al_2O_3$), which showed only 1% n-butane conversion at that temperature. At temperature of 250° C., ethane selectivity on the inventive catalyst was higher by 7% as compared to the Ir/$Al_2O_3$ catalyst.

TABLE 1

| Temp [° C.] | Ir/$Al_2O_3$ | | $MoIr_3$/$Al_2O_3$ | |
|---|---|---|---|---|
| | Conversion [%] | C2 selectivity [%] | Conversion [%] | C2 selectivity [%] |
| 250 | 10.2 | 62 | 95.7 | 69 |
| 275 | 61.3 | 60 | 100 | 60.4 |
| 300 | 100 | 60 | 100 | 34.3 |

Example 4

(Density Function Theory (DFT) Calculations)

Density function theory (DFT) calculations identified the rate-determining step (RDS) in butane hydrogenolysis as a C—C scission in the [$CH_3C$—$CCH_3$] intermediate, and the descriptor value as carbon binding energy. According to this correlation, the catalyst was predicted to have a carbon binding energy similar to carbon binding energy on Ir metal.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein can be utilized. Accordingly, the appended claims are intended to include within their scope such processes, machines, manufacture, compositions of matter, means, methods, or steps.

The invention claimed is:

1. A supported butane hydrogenolysis catalyst for hydrogenolysis of butane to ethane, the supported catalyst comprising:
   a support; and
   a crystalline catalytic bimetallic material comprising a crystalline catalytic molybdenum—iridium (Mo—Ir) composition attached to the support,
   wherein the supported catalyst has a Brunauer-Emmett-Teller (BET) surface area of 100 m$^2$/g to 150 m$^2$/g,
   wherein the supported catalyst has a butane conversion of at least 50%; and
   wherein the support comprises alumina, wherein the alumina is gamma-alumina.

2. The supported butane hydrogenolysis catalyst of claim 1, wherein the support comprises a member selected from the group consisting of zeolite, titania (TiO$_2$) and silica (SiO$_2$), or a combination thereof.

3. The supported butane hydrogenolysis catalyst of claim 2, wherein the BET surface area is 100 m$^2$/g.

4. The supported butane hydrogenolysis catalyst of claim 1, wherein the support comprises a zeolite.

5. The supported butane hydrogenolysis catalyst of claim 4, wherein the supported butane hydrogenolysis catalyst has a BET surface area of 150 m$^2$/g.

6. The supported butane hydrogenolysis catalyst of claim 4, wherein the supported butane hydrogenolysis catalyst has a BET surface area of 100 m$^2$/g.

7. The supported butane hydrogenolysis catalyst of claim 1, wherein the Mo—Ir composition has a molar ratio of Mo:Ir of 1:3 to 4:1.

8. The supported butane hydrogenolysis catalyst of claim 1, wherein the crystalline catalytic Mo—Ir composition comprises a MoIr$_3$ crystalline structure, a Mo$_3$Ir crystalline structure, or a MoIr$_4$ crystalline structure, or a mixture thereof.

9. The supported butane hydrogenolysis catalyst of claim 8, comprising 0.1 wt. % to 5 wt. % of the Mo—Ir composition having the MoIr$_3$ crystalline structure.

10. The supported butane hydrogenolysis catalyst of claim 9, comprising 0.4 wt. % to 0.8 wt. % of MoIr$_3$ on a Al$_2$O$_3$ support.

11. The supported butane hydrogenolysis catalyst of claim 10, wherein the supported butane hydrogenolysis catalyst is a 0.6 wt. % MoIr$_3$ on the Al$_2$O$_3$ support catalyst.

12. The supported butane hydrogenolysis catalyst of claim 1, wherein the supported butane hydrogenolysis catalyst has a BET surface area of 100 m$^2$/g.

13. A method to produce ethane, the method comprising contacting the supported butane hydrogenolysis catalyst of claim 1 with butane under conditions sufficient for hydrogenolysis of butane and produce ethane wherein the contacting conditions comprise a temperature of 240° C. to 325° C., a pressure of 0.35 MPa to 1.4 MPa, a butane weighted hourly velocity of 1 to 10 hr$^{-1}$, or any combination thereof.

14. The method of claim 13, wherein the conditions comprise a temperature of 260° C. to 300° C.

15. The method of claim 13, wherein the supported butane hydrogenolysis catalyst has a BET surface area of 100 m$^2$/g.

16. The method of claim 13, wherein the supported butane hydrogenolysis catalyst has a BET surface area of 150 m$^2$/g.

17. The method of claim 13, wherein the butane comprises n-butane, iso-butane, or a mixture thereof.

18. A method of producing the supported butane hydrogenolysis catalyst of claim 1, the method comprising:
    impregnating a support comprising gamma-alumina with a catalytic Mo/Ir precursor composition to form an impregnated support/Mo—Ir precursor composition material;
    drying the impregnated support/Mo—Ir precursor composition material to form a dried impregnated support/Mo—Ir precursor composition material; and
    calcining the dried impregnated support/Mo—Ir precursor composition material at a temperature of 85° C. to 100° C. for 2 to 24 hours to form the supported butane hydrogenolysis catalyst;
    wherein impregnating comprises adding the catalytic Mo/Ir precursor composition dropwise onto the support and agitating the impregnated support/catalytic Mo/Ir precursor composition for 2 to 24 hours; and heat-treating.

19. The method of claim 18, wherein the support comprises a member selected from the group consisting of gamma-alumina extrudates, a zeolite, titania extrudates, silica extrudates, or a mixture thereof.

20. A supported butane hydrogenolysis catalyst produced by the method of claim 18.

* * * * *